US012622856B2

(12) United States Patent
Hippe et al.

(10) Patent No.: US 12,622,856 B2
(45) Date of Patent: May 12, 2026

(54) AGENT FOR OXIDATIVE DYEING OF KERATIN FIBERS, CONTAINING ISATIN AND AT LEAST ONE DEFINED POLYMER

(71) Applicant: Henkel AG & Co. KGaA, Duesseldorf (DE)

(72) Inventors: Thomas Hippe, Appen (DE); Astrid Kleen, Haseldorf (DE); Hartmut Manneck, Barnitz (DE); Stefan Hoepfner, Hamburg (DE); Tugce Cansev, Hamburg (DE)

(73) Assignee: Henkel AG & Co. KGaA, Düsseldorf (DE)

( * ) Notice: Subject to any disclaimer, the term of this patent is extended or adjusted under 35 U.S.C. 154(b) by 0 days.

(21) Appl. No.: 18/884,829

(22) Filed: Sep. 13, 2024

(65) Prior Publication Data

US 2025/0009629 A1 Jan. 9, 2025

Related U.S. Application Data

(63) Continuation of application No. PCT/EP2023/050092, filed on Jan. 4, 2023.

(30) Foreign Application Priority Data

Mar. 21, 2022 (DE) ......................... 102022202756.6

(51) Int. Cl.

| | |
|---|---|
| ***A61Q 5/10*** | (2006.01) |
| ***A61K 8/34*** | (2006.01) |
| ***A61K 8/41*** | (2006.01) |
| ***A61K 8/49*** | (2006.01) |
| ***A61K 8/73*** | (2006.01) |

(52) U.S. Cl.

CPC ................ *A61K 8/492* (2013.01); *A61K 8/34* (2013.01); *A61K 8/411* (2013.01); *A61K 8/415* (2013.01); *A61K 8/73* (2013.01); *A61Q 5/10* (2013.01)

(58) Field of Classification Search

CPC .......... A61K 8/492; A61K 8/34; A61K 8/411; A61K 8/415; A61K 8/73; A61K 2800/30; A61K 2800/42; A61K 2800/4324; A61K 2800/88; A61K 8/466; A61Q 5/10

USPC ...................................................... 8/405, 406

See application file for complete search history.

(56) References Cited

U.S. PATENT DOCUMENTS

| | | | | |
|---|---|---|---|---|
| 5,261,926 A * | 11/1993 | Lang | ...................... | A61K 8/492 8/408 |
| 6,203,579 B1 * | 3/2001 | Moeller | ................... | A61Q 5/10 8/405 |
| 2017/0258695 A1 | 9/2017 | Consoli et al. | | |
| 2019/0117541 A1 | 4/2019 | Consoli et al. | | |

FOREIGN PATENT DOCUMENTS

| | | | | |
|---|---|---|---|---|
| DE | 2716671 A1 | 10/1978 | | |
| DE | 4314318 A1 * | 11/1994 | ............... | A61Q 5/10 |
| DE | 69203003 T2 | 11/1995 | | |
| DE | 19717282 A1 * | 10/1998 | ............... | A61Q 5/10 |
| DE | 19932567 A1 * | 1/2001 | ............... | A61Q 5/10 |
| DE | 102005039456 A1 | 2/2007 | | |
| EP | 1362579 A1 * | 11/2003 | ............... | A61Q 5/10 |
| EP | 1705227 A2 * | 9/2006 | ............... | A61Q 5/10 |
| EP | 2559456 B1 | 9/2018 | | |
| EP | 3943161 A1 | 1/2022 | | |
| KR | 20060073522 A * | 6/2006 | ............... | A61Q 5/10 |
| WO | WO 9524886 A1 * | 9/1995 | ............... | A61Q 5/10 |
| WO | 9847472 A1 | 10/1998 | | |

OTHER PUBLICATIONS

Anonymous: "Description of a Proposed Reference Dose Resorcinol", Sep. 1, 2004 (Sep. 1, 2004), XP055300873, Gefunden im Internet: URL:http://www.dep.State.pa.US/dep/subject /advcoun/cleanup/2004/Dec8/AMEC_Resorcinol RFD_090804.pdf [gefunden am Sep. 8, 2016] Executive summary, ES-2 Hazard Identification, 3. Use of resorcinol, 5. Hazard identification, 5.1. Human.

PCT International Search Report—WO PCT/EP2023/050092—Completed: Apr. 14, 2023; Mailing date: Apr. 24, 2023—Number of pp. 149.

* cited by examiner

*Primary Examiner* — Eisa B Elhilo

(74) *Attorney, Agent, or Firm* — Blank Rome LLP

(57) ABSTRACT

An agent for oxidatively dyeing keratin fibers, in particular human hair, containing, in a cosmetic carrier, isatin and at least one polymer from the group consisting of xanthan gum, algin, carrageenan, cetyl hydroxyethyl cellulose, carboxymethyl cellulose, tragacanth, gum karaya, gum ghatti, agar, chitin, chitosan, gum arabic, gellan gum, guar gum, tamarind seed flour, carob gum, and the physiologically acceptable salts thereof.

18 Claims, No Drawings

AGENT FOR OXIDATIVE DYEING OF KERATIN FIBERS, CONTAINING ISATIN AND AT LEAST ONE DEFINED POLYMER

FIELD OF INVENTION

The present invention relates to cosmetic agents for oxidatively dyeing keratin fibers, which comprise isatin (a) and at least one polymer (b) from the group consisting of xanthan gum, algin, carrageenan, cetyl hydroxyethyl cellulose, carboxymethyl cellulose, tragacanth, gum karaya, gum ghatti, agar, chitin, chitosan, gum arabic, gellan, guar, tamarind seed flour, carob gum, and physiologically tolerated salts thereof.

A further object is a method for the oxidative dyeing of keratin fibers, in which a previously described agent is applied to the keratin fibers and rinsed out again after an exposure time.

BACKGROUND

To provide color-changing cosmetic agents—in particular, for keratin fibers, such as hair—a person skilled in the art is aware of various dyeing systems, depending upon the dyeing requirement. So-called oxidative dyeing agents are used for permanent, intense coloring having appropriate fastness properties. Such dyes typically contain oxidation dye precursors, known as developer components, and coupler components, which together form the actual dyes under the influence of oxidizing agents—for example, hydrogen peroxide. Oxidative dyeing agents are characterized by outstanding, long-lasting coloring results.

The oxidation dye precursors (developers and couplers) themselves are not colored, but, rather, the actual dyes are only formed during application as a result of the oxidation dye precursors coming into contact with the oxidizing agent (hydrogen peroxide). In a chemical reaction, the developers used as oxidation dye precursors (such as p-phenylenediamine or its derivatives) are first oxidatively converted by hydrogen peroxide into a reactive intermediate, also called quinonimine or quinone diimine, which then reacts in an oxidative coupling reaction with the couplers to form the corresponding dye.

With oxidative dyeing agents, hair can be dyed both in intensive mode shades and in natural shades by choosing the suitable developer components and coupler components. A large area of application for the oxidative dyeing agents is the coloring of gray hair in a natural shade, which resembles the hair color that the user had when they were younger. A person skilled in the art is aware of the use of developers based upon the base body of 1,4-diaminobenzene (para-phenylenediamine) and couplers with resorcinol structure (1,3-dihydroxybenzene) as a classic combination for the generation of oxidative dyeing in the brown to dark-blonde range.

Said oxidation dyes have been used for decades. Although they are intended only for extracorporeal use on keratin fibers such as head hair, eyelashes, and eyebrows, contact of the dyeing agent with the scalp cannot be completely avoided during use. In order to ensure the highest possible product safety for customers, the commercially available oxidation dye precursors are continuously checked for their physiological compatibility—for example, by the Scientific Committee on Consumer Products (SCCP), an advisory body of the European Commission. It is known that some of the oxidation dye precursors, and in particular some of the para-phenylenediamine-type oxidation bases, can have a certain sensitization potential. The customer is therefore advised to perform a preliminary test with a small amount of the dyeing agent on the skin before using the dyeing agent on the hair in order to preclude allergic reactions during or after the dyeing process. In addition to skin sensitization, other physiological effects are also monitored.

Said oxidation dyes have been used for decades. Although they are intended only for extracorporeal use on keratin fibers such as head hair, eyelashes, and eyebrows, contact of the dyeing agent with the scalp cannot be completely avoided during use. In order to ensure the highest possible product safety for customers, the commercially available oxidation dye precursors are continuously checked for their physiological compatibility—for example, by the Scientific Committee on Consumer Products (SCCP), an advisory body of the European Commission. It is known that some of the oxidation dye precursors, and in particular some of the para-phenylenediamine-type oxidation bases, can have a certain sensitization potential. The customer is therefore advised to perform a preliminary test with a small amount of the dyeing agent on the skin before using the dyeing agent on the hair in order to preclude allergic reactions during or after the dyeing process. In addition to skin sensitization, other physiological effects are also monitored.

Resorcinol, 4-chlororesorcinol, and 2-methylresorcinol are common oxidation dye precursors having a 1,3-dihydroxybenzene base body. In its last opinion of March 2021, SCCP came to the conclusion that the use of resorcinol in oxidative hair dyes at a resorcinol concentration of up to 1.25 wt % in the ready-to-use mixture was considered safe. The SCCP stated that resorcinol has a thyroid-inhibiting effect. Although a clear level of exposure required for such effect cannot be derived from the available studies in humans, most of these studies indicate a relatively much higher exposure than is the case in cosmetics.

SUMMARY OF THE INVENTION

In order to take into account the concerns of some consumers with regard to product safety, the object of the present invention was to provide an agent for oxidatively dyeing keratin fibers, and in particular human hair, with which a broad color spectrum can be covered, and in particular a natural color palette with cool natural shades and warm natural shades, and a gold color series which results in colors having high fastness properties, without impairing product safety. In particular, dyeing in these natural shades should be possible without the use of couplers of the recyclin type.

Many users dye their hair in the same shade over decades and do not wish for a sudden, obviously visible, change to their usual hair color. For these users, it is therefore essential to allow the customary, resorcinol-containing hair dye to be replaced by a new, resorcinol-free product without a shift in shade. A central challenge of the present application was therefore to find a new, resorcinol-free hair dye which, in its color loss and its color result, corresponds as precisely as possible to the resorcinol-containing dyeing agent used to date.

Surprisingly, it has now been found that this object can be achieved excellently by an oxidative dyeing agent containing isatin (a) and at least one polymer (b) from the group consisting of xanthan gum, algin, carrageenan, cetyl hydroxyethyl cellulose, carboxymethyl cellulose, tragacanth, gum karaya, gum ghatti, agar, chitin, chitosan, gum arabic, gellan, guar, tamarind seed flour, carob gum, and physiologically tolerated salts thereof.

DETAILED DESCRIPTION OF THE INVENTION

A first subject matter of the present invention is therefore an agent for oxidatively dyeing keratin fibers, and in particular human hair, containing, in a cosmetic carrier, (a) isatin and (b) at least one polymer from the group consisting of xanthan gum, algin, carrageenan, cetyl hydroxyethyl cellulose, carboxymethyl cellulose, tragacanth, gum karaya, gum ghatti, agar, chitin, chitosan, gum arabic, gellan, guar, tamarind seed flour, carob gum, and physiologically tolerated salts thereof.

The work leading to this invention has shown that the oxidative dyeing of hair using isatin (a) leads to very intense dyeing with excellent fastness properties if a certain polymer from the above-mentioned group (b) is still contained in the dyeing agent.

Keratin Fibers

Keratin fibers are in principle understood to mean all types of animal hair, e.g., wool, horsehair, angora hair, furs, feathers, and products or textiles manufactured therefrom. Preferably, however, the keratin fibers are human hair.

Agents for Oxidative Dyeing

The term, "agents for oxidative dyeing," of keratin fibers used according to the invention is understood to mean oxidative dyeing agents. Such dyeing agents contain oxidation dye precursors, so-called developer components, and coupler components. Developers and couplers diffuse separately into the keratin fibers and, in a chemical reaction with one another, form the actual dyes under the influence of an alkalizing agent (e.g., ammonia) and an oxidizing agent (hydrogen peroxide). Depending upon the quantity of oxidizing agent employed, the keratin fibers are simultaneously lightened to a greater or less extent during coloring, since the oxidizing agent not only initiates the dye-forming process of the developers and couplers, but also oxidatively destroys the hair's own pigments (melanins). Depending upon the used amounts of the oxidation dye precursor products and of the oxidizing agent, the oxidative dyeing can therefore be predominantly a coloration (with high dye proportion) or predominantly a lightening (with high proportion of oxidizing agent). In the latter case, the oxidation dye precursors are mostly used for shading the brightening result.

The agents according to the invention contain the constituents essential to the invention in a cosmetic carrier, and preferably in a suitable aqueous, alcoholic, or aqueous-alcoholic carrier. For the purpose of hair coloring, such carriers are for example creams, emulsions, gels, or also surfactant-containing foaming solutions, such as for example shampoos, foam aerosols, form formulations, or other preparations which are suitable for application to hair.

The oxidative dyeing agent described above is a ready-to-use dyeing agent which is applied in this form containing the components (a) and (b) for application to the keratin fibers.

Isatin

As a first component essential to the invention, the oxidative dyeing agent is isatin (a). Isatin is the compound of formula (ISA), which can alternatively also be referred to as 2,3-indoline-dione or as 2,3-dioxoindoline (ISA)

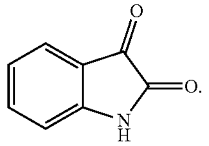

Isatin has the CAS number 91-56-5.

With regard to an optimal solution of the object according to the invention, isatin (a) is preferably contained in specific quantity ranges in the agent according to the invention. Particularly positive results were obtained when the agent contained—relative to the total weight of the agent—0.001 to 10 wt %, preferably 0.01 to 5 wt %, more preferably 0.1 to 3.5 wt %, and very particularly preferably 0.15 to 2.5 wt % isatin (a).

In a particularly preferred embodiment, an agent according to the present invention is thus characterized in that it contains, relative to the total weight of the agent, 0.001 to 10 wt %, preferably 0.01 to 5 wt %, more preferably 0.1 to 3.5 wt %, and particularly preferably 0.15 to 2.5 wt % isatin (a).

Isatin is commercially available from different suppliers, such as Acros, Sigma Aldrich, Thermo Scientific, etc.

Polymers (b)

As a second component (b) essential to the invention, the dyeing agent according to the invention contains at least one polymer from the group consisting of xanthan gum, algin, carrageenan, cetyl hydroxyethyl cellulose, carboxymethyl cellulose, tragacanth, gum karaya, gum ghatti, agar, chitin, chitosan, gum arabic, gellan, guar, tamarind seed flour, carob gum, and physiologically tolerated salts thereof.

Xanthan gum is a polysaccharide composed, inter alia, of the structural components D-glucose, D-mannose, D-glucuronic acid, acetate, and pyruvate and is also known by the INCI name, xanthan gum. Xanthan gum bears carboxyl groups and is anionic or anionizable. The physiologically tolerated salts of xanthan gum are also in accord with the invention. Xanthan is sold commercially by CP Kelco, for example, under the trade name, Keltrol TF.

The salts of alginic acid are referred to as alginates (INCI name algin). Alginic acid is alternatively also referred to as algin. Alginates are acidic, carboxyl-group-containing polysaccharides, consisting of D-mannuronic acid and D-guluronic acid in different ratios linked by 1-4 glycosidic linkages. The alkali metal salts and the alkaline earth metal salts of the alginic acids are in particular in accord with the invention. The use of alginic acid, sodium alginate, potassium alginate, ammonium alginate, and/or calcium alginate has proven particularly advantageous. The sodium salt of alkyne can be purchased from Kelco under the trade name, Kelgin F, from Kelco.

Carrageen is also referred to synonymously as carrageenan. Carrageen is a sulfated galactan, which can be extracted from red algae, for example. The carrageenan precipitated from the hot water extract of algae is a colorless to sand-colored powder having a molecular weight of 100,000-800,000 and a sulfate content of about 25%, which is very easily soluble in warm water. Carrageenan is divided into three main components having different properties: κ-carrageenan, ι-carrageenan, and λ-carrageenan. The gel-forming κ fraction consists of d-galactose-4-sulfate and 3,6-anhydro-α-d-galactose, which are alternately glycosidically linked at the 1,3 and 1,4 positions. The non-gelling λ fraction is composed of 1,3-glycosidically linked d-galactose-2-sulfate and 1,4-linked d-galactose-2,6-disulfate residues and is readily soluble in cold water. The ι-carrageenan composed of d-galactose-4-sulfate in 1,3-linkage and 3,6-anhydro-α-d-galactose-2-sulfate in 1,4-linkage is soluble in hot water and also gel-forming.

Cetyl hydroxyethyl cellulose is alternatively also referred to as hexadecylhydroxyethyl cellulose, is a hydrophobically-modified hydroxyethyl cellulose, which has the CAS number 80455-45-4. Cetyl hydroxyethyl cellulose is a non-ionic associative polymer, which carries both hydroxyalkyl groups and long-chain alkyl groups. Cetyl hydroxyethyl cellulose can be purchased from Ashland, for example, under the trade name, Natrosol Plus 330 CS.

Carboxymethyl celluloses are cellulose ethers—derivatives of cellulose in which a portion of the hydroxyl groups is linked as ether to a carboxymethyl group (—CH2-COOH). In the form of the free acid, carboxymethyl cellulose has the CAS number 9000-11-7, and the sodium salt has the CAS number 9004-32-4. Both the free acid and the sodium salt of the carboxymethyl cellulose accord with the invention. Carboxymethyl cellulose can be purchased commercially from Shahid Zeinoddin, for example, under the trade name, carboxymethyl cellulose sodium salt. The substance under the trade name, Tylose C 6000, is also commercially available from SE Tylose (Shin Etsu).

Tragacanth (also tragacanth gum) is a gum or a natural polysaccharide. It consists of the plant sap extracted and dried after the incision of trunks and branches of shrubby representatives of the Faboideae family Tragacanth (*Astragalus*), *Astragalus gummifer, Astragalus bustillosii*, and *Astragalus tragacantha*, as well as *Astracantha adscendens, Astracantha microcephala, Astracantha kurdica*, and *Astracantha strobilifera.*

Karaya (Indian tragacanth, karaya gum, sterculia gum, E 416) is a gum composed mainly of carbohydrates and galacturonic acid. It is an acidic polysaccharide of D-galactose, L-rhamnose, D-galacturonic acid, D-glucuronic acid, and acetic acid.

Gum ghatti or also Indian rubber is a polysaccharide from the exudate of the bark of the *Anogeissus liatifolia* (Combretaceae) tree found in India and Sri Lanka. The properties of gum ghatti are similar to those of gum arabic. 80-90% of the gum ghatti is soluble or dispersible in water; however, the aqueous solutions have a higher viscosity. Gum ghatti has the CAS number 9000-28-6 and can be purchased, for example, from the supplier, Biynth Carbynth.

Agar, which is also called agar-agar, is a galactose polymer and thus a polysaccharide that can form jellies. The base units of agar are agarose and sulfated agaropectin. Agar is prepared from the cell walls of some types of algae (especially red algae, such as *Gracilaria, Gelidiopsis, Gelidium, Hypnea*, and *Sphaerococcus* species), mainly from East Asia.

Chitin is a polysaccharide composed of acetylglucosamine units (more precisely: 2-acetamido-2-deoxy-D-glucopyranose, shortened to: N-acetyl-D-glucosamine, abbreviation: GlcNAc). The acetylglucosamine units are linked by β-1,4-glycosidic linkages. Chitin can thus be understood as a variant of cellulose in which the hydroxyl groups in position 2 of the monomer units have been replaced by acetamido groups.

Chitosan, also referred to as poliglusam or poly-D-glucosamine or polyglucosamine, is a naturally-occurring biopolymer derived from chitin that is composed of β-1,4-glycosidically-linked N-acetylglucosamine residues (more specifically, 2-acetamido-2-deoxy-β-d-glucopyranose residues) and is thus, like said chitin, a polyaminosaccharide. For the preparation of chitosan, chitin is deacetylated, so that the molecule finally consists only of approximately 2,000 linear 2-amino-2-deoxy-β-D-glucopyranose or glucosamine monomers linked to one another in a linear manner.

Gum arabic refers to the rubber from the exudate of various *Acacia* trees distributed throughout Africa and species such as the gum arabic tree (*Senegalia senegal*) and *Acacia nilotica* (*Vachellia nilotica*), the red *acacia* (*Vachellia seyal*) and *Vachellia tortilis, Vachellia gummifera, Vachellia karroo*, and the Robber-thorn (*Vachellia horrida*).

Gellan gum belongs to the linear polysaccharides and consists of several different building blocks. It consists of one rhamnose, one glucuronic acid, and two glucose base units esterified with acetic acid and glyceric acid. The glucuronic acid is present as a mixed potassium, calcium, sodium, and magnesium salt. The molar mass is approximately 500,000 g/mol.

The guar bean (*Cyamopsis tetragonoloba*), also referred to as guar or cluster bean, is a cultivated plant in the legume family (Fabaceae or Leguminosae), subfamily Faboideae. It is closely related to a number of other field fruits called "beans." The most important product of the plant is guar gum (also referred to as guar, guar flour), which consists mainly of the polysaccharide guar. To produce guar gum, the outer layers and the seedling are separated from the seed before it is ground.

Tamarind seed flour is the product of the seeds of the tamarind. These contain complex carbohydrates (polysaccharides or hydrocolloids), which are used primarily as gelling and thickening agents. Tamarind seed flour can be isolated by extraction with hot water and subsequent drying. The main components of these polysaccharides are—in addition to arabinose—galactose, xylose, and glucose. Locust bean gum is a polysaccharide composed mostly of galactose (20%) and mannose (80%).

Particularly intense and natural colorations were obtained with oxidative dyeing agents which contained isatin (a) and at least one polymer (b) selected from the group consisting of xanthan, algin, carrageenan, cetyl hydroxyethyl cellulose, carboxymethyl cellulose, and physiologically tolerated salts thereof. The use of the polymers from this specific group is therefore very particularly preferred.

In a further very particularly preferred embodiment, an agent according to the invention is characterized in that it contains at least one polymer (b) selected from the group consisting of xanthan, algin, carrageenan, cetyl hydroxyethyl cellulose, carboxymethyl cellulose, and physiologically tolerated salts thereof.

Physiologically tolerated salts of polymers (b) are all salts which can be applied to the body under physiological conditions in the field of cosmetics. Particularly well-suited physiologically tolerated salts are in particular the sodium salts, the potassium salts, and the ammonium salts of the polymers (b).

The polymer(s) (b) are preferably used in specific quantity ranges in the agent according to the invention. The agent preferably contains, relative to the total weight of the agent, one or more polymers (b) in a total amount of 0.01 to 10.0 wt %, preferably 0.1 to 5.0 wt %, more preferably 0.2 to 2.5 wt % and very particularly preferably 0.3 to 1.5 wt %.

In the context of another very particularly preferred embodiment, an agent according to the invention is characterized in that the agent contains, relative to the total weight of the agent, one or more polymers (b) in a total amount of 0.01 to 10.0 wt %, preferably 0.1 to 5.0 wt %, more preferably 0.2 to 2.5 wt %, and very particularly preferably 0.3 to 1.5 wt %.

Oxidation Dye Precursors of Developer Type (a)

Oxidative dyeing agents contain oxidation dye precursors, so-called developers, and coupler components to form the coloring. Developers and couplers diffuse separately into the keratin fibers and form the actual dyes in a chemical reaction with one another under the influence of ammonia as alkalizing agent and an oxidizing agent. Depending upon the quantity of oxidizing agent employed, the keratin fibers are simultaneously lightened to a greater or less extent during coloring, since the oxidizing agent not only initiates the dye-forming process of the developers and couplers, but also oxidatively destroys the hair's own pigments (melanins). Depending upon the used amounts of the oxidation dye precursor products and of the oxidizing agent, the oxidative dyeing can therefore be predominantly a coloration (with high dye proportion) or predominantly a lightening (with high proportion of oxidizing agent). In the latter case, the oxidation dye precursors are mostly used for shading the brightening result.

Particularly preferably, the oxidative dyeing agents according to the invention additionally contain isatin (a) at least one oxidation dye precursor of developer type (c), also referred to as developer for short.

Particularly suitable oxidation dye precursors of the developer type are selected from the group consisting of p-toluenediamine, 2-methoxymethyl-p-phenylenediamine, 2-(2-hydroxyethyl)-p-phenylenediamine, N,N-bis-(2-hydroxyethyl)-p-phenylenediamine, p-phenylenediamine, and physiologically tolerated salts thereof.

In a particularly preferred embodiment, an agent according to the invention is therefore characterized in that it contains at least one oxidation dye precursor of developer type (c) which is selected from the group consisting of p-toluene diamine, 2-methoxymethyl-p-phenylenediamine, 2-(2-hydroxy-ethyl)-p-phenylenediamine, N,N-bis-(2-hydroxyethyl)-p-phenylenediamine, p-phenylenediamine, and physiologically tolerated salts thereof. p-toluene diamine is alternatively also referred to as 2,5-toluenediamine, p-toluenediamine (abbreviation: PTD), 2,5-diaminotoluene, 2-methyl-p-phenylenediamine, or 2,5-diaminomethylbenzene. PTD has the CAS number 95-70-5. 2-methoxymethyl-p-phenylenediamine is alternatively also referred to as 2-methoxymethyl-1,4-benzenediamine and in the form of its free base has the CAS number 337906-36-2. 2-(2-hydroxyethyl)-p-phenylenediamine is alternatively to referred as 2-(2,5-diaminophenyl)ethanol and in the form of its free base has the CAS number 93841-24-8. N,N-bis-(2-hydroxyethyl)-p-phenylenediamine in the form of its free base has the CAS number 7575-35-1.

With an oxidative dyeing agent containing a developer (c) of the aforementioned group with basic structure of the 1,4-diaminobenzene, hair can be dyed with very high intensity in natural shades, and in particular in dark brown, medium brown, and dark flash shades. It was also particularly surprising that the hair could be colored in a shade which was particularly strongly similar to the shade obtained with a dyeing agent containing the classic combination of PDT and resorcinol.

The agents which contain at least one oxidation dye precursor of the developer type (c), which is selected from the group of p-toluenediamine, 2-methoxymethyl-p-phenylenediamine, and the physiologically tolerated salts thereof, have proven to be very particularly suitable for achieving the object according to the invention.

In a particularly preferred embodiment, an agent according to the invention is therefore characterized in that it contains at least one oxidation dye precursor of developer type (c) which is selected from the group of p-toluenediamine, 2-methoxymethyl-p-phenylenediamine, and the physiologically tolerated salts thereof.

However, the agent according to the invention can also contain other developers (c) to form shades with a reddish natural tone. For example, developers from the group consisting of 4-amino-3-methylphenol, p-aminophenol, 4,5-diamino-1-(2-hydroxyethyl)pyrazole, and the physiologically tolerated salts thereof are suitable for this purpose. These developers can be used either as a group on their own or also together with one or more developers having a basic structure of p-phenylenediamine.

In a further preferred embodiment, an agent according to the invention is therefore characterized in that it contains at least one oxidation dye precursor of developer type (c) which is selected from the group consisting of 4-amino-3-methylphenol, p-aminophenol, 4,5-diamino-1-(2-hydroxyethyl)pyrazole, and the physiologically tolerated salts thereof.

In a further very particularly preferred embodiment, an agent according to the invention is therefore characterized in that it contains at least one oxidation dye precursor of developer type (c) which is selected from the group consisting of p-toluenediamine, 2-methoxymethyl-p-phenylenediamine, 2-(2-hydroxy-ethyl)-p-phenylenediamine, N,N-bis-(2-hydroxyethyl)-p-phenylenediamine, p-phenylenediamine, 4-amino-3-methylphenol, p-aminophenol, 4,5-diamino-1-(2-hydroxyethyl)pyrazole, and the physiologically tolerated salts thereof.

The developers of the above-mentioned groups can be used in the agent according to the invention in the form of their free base or else in the form of their physiologically tolerated salts. A physiologically tolerated salt is understood to mean a salt of the developer that is well tolerated by the user under physiological conditions, i.e., during use of the agent. Physiologically tolerated salts are in particular the chlorides, bromides, sulfates, and hemisulfates of developers (c).

In a further particularly preferred embodiment, an agent according to the invention is therefore characterized in that it contains at least one oxidation dye precursor of developer type (c), which is selected from the group of p-toluenediamine, p-toluenediamine sulfate, p-toluenediamine chloride, p-toluenediamine bromide, 2-methoxymethyl-p-phenylenediamine, 2-methoxymethyl-p-phenylenediamine sulfate, 2-methoxymethyl-p-phenylenediamine chloride and 2-methoxymethyl-p-phenylenediamine bromide, 4,5-diamino-1-(2-hydroxyethyl)pyrazole chloride, 4,5-diamino-1-(2-hydroxyethyl)pyrazole bromide, and 4,5-diamino-1-(2-hydroxyethyl) pyrazole sulfate.

Depending upon the desired color effect, it can furthermore be preferred for the agent to additionally contain one or more further oxidation dye precursors of the developer type which are selected from the group of bis-(2-hydroxy-5-aminophenyl)methane, 1,3-bis-(2,5-diaminophenoxy)propan-2-ol, N,N'-bis-(4-aminophenyl)-1,4-diazacycloheptane, 1,10-bis-(2,5-diaminophenyl)-1,4,7,10-tetraoxadecane, 4-amino-2-aminomethylphenol, 4-amino-2-(1,2-dihydroxyethyl)phenol, 4-amino-2-(diethylaminomethyl)phenol, 2,4,5,6-tetraaminopyrimidine, 4-hydroxy-2,5,6-triaminopyrimidine, 2-hydroxy-4,5,6-triaminopyrimidine, 2,3-diamino-6,7-dihydro-1H, 5H-pyrazolo[1,2-a]pyrazol-1-one, and the physiologically tolerated salts thereof.

Preferably, the developer(s) are used in certain quantity ranges in the agent according to the invention. The agent preferably contains, relative to the total weight of the agent, one or more oxidation dye precursors of developer type (c) in a total amount of 0.001 to 10.0 wt %, preferably 0.01 to 6.0 wt %, more preferably 0.1 to 5.0 wt %, and very particularly preferably 0.15 to 4.7 wt %.

In a particularly preferred embodiment, an agent according to the invention is thus characterized in that the agent contains, relative to the total weight of the agent, one or more oxidation dye precursors of developer type (c) in a total amount of 0.001 to 10.0 wt %, preferably 0.01 to 6.0 wt %, more preferably 0.1 to 5.0 wt %, and very particularly preferably 0.15 to 4.7 wt %.

Further Couplers (d) in Oxidative Dyeing Agents

For precise shading and/or fine adjustment of the desired hue, the oxdiactive dyeing agent can, in addition to isatin (a) and, optionally, the oxidation dye precursors of developer type (c), also contain further couplers (d).

Further very well-suited couplers can be selected, for example, from the group comprising 3-aminophenol, 5-amino-2-methylphenol, 3-amino-2-chloro-6-methylphenol, 2hydroxy-4-aminophenoxyethanol, 5-amino-4-chloro-2-methylphenol, 5-(2-hydroxyethyl)amino-2-methylphenol, 2,4-dichloro-3-aminophenol, 2-aminophenol, 3-phenylenediamine, 2(2,4-diaminophenoxy)ethanol, 1,3-bis(2,4-diaminophenoxy)propane, 1-methoxy-2-amino-4-(2-hydroxyethylamino)benzene, 1,3-bis-(2,4-diaminophenyl)propane, 2,6-bis(2'-hydroxyethyl)-1-methylbenzene, 1-amino-3-bis-(2-hydroxyethyl)aminobenzene, 2-amino-3-hydroxypyridine, 3-amino-2-methylamino-6-methoxypyridine, 2,6-dihydroxy-3,4-dimethylpyridine, 3,5-diamino-2,6-dimethoxypyridine, 1-phenyl-3-methylpyrazol-5-one, 1-naphthol, 1,5-dihydroxynaphthalene, 2,7-dihydroxynaphthalene, 1,7dihydroxynaphthalene, 1,8-dihydroxynaphthalene, 4-hydroxyindole, 6-hydroxyindole, 7hydroxyindole, 4-hydroxyindoline, 6-hydroxyindoline, 7-hydroxyindoline, or mixtures of said compounds or the physiologically tolerated salts thereof.

In a particularly preferred embodiment, an agent according to the invention is thus characterized in that it contains at least one oxidation dye precursor of coupler type (d), which is selected from the group of 3-aminophenol, 5-amino-2-methylphenol, 3-amino-2-chloro-6-methylphenol, 2-hydroxy-4-aminophenoxyethanol, 5-amino-4-chloro-2-methylphenol, 5-(2-hydroxyethyl)-amino-2-methylphenol, 2,4-dichloro-3-aminophenol, 2-aminophenol, 3-phenylenediamine, 2-(2,4-diaminophenoxy)ethanol, 1,3-bis(2,4-diaminophenoxy)propane, 1-methoxy-2-amino-4-(2-hydroxyethylamino)benzene, 1,3-bis-(2,4-diaminophenyl)propane, 2,6-bis(2'-hydroxyethylamino)-1-methylbenzene, 1-amino-3-bis-(2-hydroxyethyl) aminobenzene, 2-amino-3-hydroxypyridine, 3-amino-2-methylamino-6-methoxypyridine, 2,6-dihydroxy-3,4-dimethylpyridine, 3,5-diamino-2,6-dimethoxypyridine, 1-phenyl-3-methylpyrazol-5-one, 1-naphthol, 1,5-dihydroxynaphthalene, 2,7-dihydroxynaphthalene, 1,7-dihydroxynaphthalene, 1,8-dihydroxynaphthalene, 4-hydroxyindole, 6-hydroxyindole, 7-hydroxyindole, 4-hydroxyindolin, 6-hydroxyindolin, 7-hydroxyindolin, or mixtures of said compounds or the physiologically tolerated salts thereof.

Particularly natural shades with great similarity to the corresponding resorcinol-containing dyes could be obtained if the dyeing agent additionally contained one or more couplers (d) which were selected from the group consisting of 3-aminophenol, 5-amino-2-methylphenol, 3-amino-2-chloro-6-methylphenol, 2-amino-3-hydroxypyridine, 1-methoxy-2-amino-4-(2-hydroxyethylamino)benzene, 6-hydroxyindole, or mixtures of these compounds or the physiologically tolerated salts thereof. For this reason, the use of couplers (d) from this group is explicitly very particularly preferred.

In an explicitly very particularly preferred embodiment, an agent according to the invention is therefore characterized in that it contains at least one oxidation dye precursor of coupler type (d) selected from the group consisting of 3-aminophenol, 5-amino-2-methylphenol, 3-amino-2-chloro-6-methylphenol, 2-amino-3-hydroxypyridine, 1-methoxy-2-amino-4-(2-hydroxyethylamino)benzene, 6-hydroxyindole, or mixtures of said compounds or the physiologically tolerated salts thereof.

The couplers from the above-described group (d) are also preferably used in specific quantity ranges in the agent according to the invention. Particularly positive results were obtained when the agent contained, relative to the total weight of the agent, one or more oxidation dye precursors of coupler type (d) in a total amount of 0.001 to 10 wt %, preferably 0.01 to 5 wt %, more preferably 0.1 to 3.5 wt %, and very particularly preferably 0.15 to 2.5 wt %.

In a particularly preferred embodiment, an agent according to the invention is characterized in that the agent contains, relative to the total weight of the agent, one or more oxidation dye precursors of coupler type (d) in a total amount of 0.001 to 10 wt %, preferably 0.01 to 5 wt %, more preferably 0.1 to 3.5 wt %, and very particularly preferably 0.15 to 2.5 wt %.

Dispensing With Resorcinol-Type Couplers

As already described above, with the agents of the present application, intense colorations in the natural tone range should be developed, which give rise to the shades that are produced with resorcinol-containing dyeing agents as well as possible without being dependent upon the use of couplers of the resorcinol type.

Resorcinol-type couplers or couplers from the group of resorcinols are understood to mean 1,3-dihydroxybenzene and its derivatives. Derivatives of 1,3-dihydroxybenzene are all compounds which have a 1,3-dihydroxybenzene basic structure and carry further substituents, but both hydroxyl groups of the 1,3-dihydroxybenzene must still be present.

The couplers from the group of resorcinols standardly used in market products are resorcinol, 2-methylresorcinol, and 4-chlororesorcinol. Couplers from the group of resorcinols are therefore understood in particular to be resorcinol, 2-methylresorcinol, and 4-chlororesorcinol. In the agents of the present application, these couplers are to be dispensed with, and therefore it is preferred if the total amount of oxidative dye precursors of the coupler type contained in the agent from the group of resorcinols, and particularly from the group consisting of resorcinol, 2-methylresorcinol, and 4-chlororesorcinol, is below 0.1 wt %, preferably below 0.05 wt %, particularly preferably below 0.01 wt %, and very particularly preferably 0 wt %.

In a further very particularly preferred embodiment, an agent according to the invention is therefore characterized in that, relative to the total weight of the agent, the total amount of the oxidation dye precursors of the coupler type contained in the agent from the group of resorcinols, and in particular from the group consisting of resorcinol, 2-methylresorcinol, and 4-chlororesorcinol, is below 0.1 wt %, preferably below 0.05 wt %, particularly preferably below 0.01 wt %, and very particularly preferably 0 wt %.

Direct Dyes

Furthermore, the agents according to the invention can optionally contain at least one direct dye. These are dyes which are drawn directly onto the hair and which do not require an oxidative process in order to form the color. Direct dyes are usually nitrophenylenediamines, nitroaminophenols, azo dyes, anthraquinones, triarylmethane dyes, or indophenols.

The direct dyes are each used preferably in an amount of 0.001 to 20 wt %, and in particular 0.05 to 5 wt %, in each case in relation to the total preparation for use. The total quantity of direct dyes is preferably at most 3 wt %.

Direct dyes can be divided into anionic, cationic, and non-ionic direct dyes, which are selected and used by a person skilled in the art according to the requirements of the support base.

Preferred anionic direct dyes are the compounds known under the international names or trade names, Acid Yellow 1, Yellow 10, Acid Yellow 23, Acid Yellow 36, Acid Orange 7, Acid Red 33, Acid Red 52, Pigment Red 57:1, Acid Blue 7, Acid Green 50, Acid Violet 43, Acid Black 1, and Acid Black 52.

Preferred cationic direct dyes are Basic Blue 7, Basic Blue 26, Basic Violet 2 und Basic Violet 14, Basic Yellow 57, Basic Red 76, Basic Blue 16, Basic Blue 347 (Cationic Blue 347/Dystar), HC Blue No. 16, Basic Blue 99, Basic Brown 16, Basic Brown 17, Yellow 87, Basic Orange 31, and Basic Red 51.

In particular, non-ionic nitro dyes and quinone dyes and neutral azo dyes are suitable as non-ionic direct dyes. Preferred non-ionic direct dyes are the compounds known under the international names or trade names, HC Yellow 2, HC Yellow 4, HC Yellow 5, HC Yellow 6, HC Yellow 12, HC Orange 1, Disperse Orange 3, HC Red 1, HC Red 3, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9, and also 1,4-diamino-2-nitrobenzene, 2-amino-4-nitrophenol, 1,4-bis(2-hydroxyethyl)amino-2-nitrobenzene, 3-nitro-4-(2-hydroxy-ethyl)aminophenol, 2-(2-hydroxyethyl)amino-4,6-dinitrophenol, 4-[(2-hydroxyethyl)amino]-3-nitro-1-methylbenzene, 1-amino-4-(2-hydroxyethyl)amino-5-chloro-2-nitrobenzene, 4-amino-3-nitrophenol, 1-(2'-ureidoethyl) amino-4-nitrobenzene, 2-[(4-amino-2-nitrophenyl)amino] benzoic acid, 6-nitro-1,2,3,4-tetrahydroquinoxaline, 2-hydroxy-1,4-naphthoquinone, picramic acid and salts thereof, 2-amino-6-chloro-4-nitrophenol, 4-ethylamino-3-nitrobenzoic acid, and 2-chloro-6-ethylamino-4-nitrophenol.

Hydrogen Peroxide (e)

For the formation of the colors in the oxidative dyeing process, the oxidative dyeing agent according to the invention preferably contains at least one oxidizing agent (e) which is particularly preferably hydrogen peroxide and/or the addition products of hydrogen peroxide to organic or inorganic compounds.

In a preferred embodiment, hydrogen peroxide itself is used as an aqueous solution in the oxidative dyeing agent. The concentration of a hydrogen peroxide solution is determined by the legal requirements, on one hand, and by the desired effect, on the other; preferably, 6 to 12 wt % solutions in water are used. Oxidative preferred according to the present invention are characterized in that they contain 0.5 to 20 wt %, preferably 1 to 12.5 wt %, especially preferably 2.5 to 10 wt %, and, in particular, 3 to 8 wt % hydrogen peroxide, relative in each case to the total weight of the oxidative dyeing agent.

In a further particularly preferred embodiment, an agent according to the invention is therefore characterized in that it contains at least one oxidizing agent (e) from the group consisting of hydrogen peroxide and addition products thereof to organic or inorganic compounds.

In a particularly preferred embodiment, an agent according to the present invention is characterized in that it contains, relative to the total weight of the agent, 0.5 to 20 wt %, preferably 1 to 12.5 wt %, more preferably 2.5 to 10 wt %, and particularly preferably 3 to 8 wt % hydrogen peroxide (e).

Alkalizing Agent

Coloring processes on keratin fibers typically take place in an alkaline environment. To protect the keratin fibers as well as the skin as much as possible, however, it is not desirable to adjust to too high a pH value. It is therefore preferred if the pH of the ready-to-use agent is between 6 and 11, and in particular between 7 and 10.5. The pH values in the sense of the present invention are pH values which have been measured at a temperature of 22° C.

The work leading to this invention has shown that good color results were obtained in particular if an alkalizing agent from the group consisting of ammonia, monoethanolamine, 2-amino-2-methylpropanol, arginine, lysine, ornithine, and histidine was used in the dyeing agent according to the invention. For this reason, the dyeing agent according to the invention contains as a third substantial ingredient at least one alkalizing agent (f) from the group consisting of ammonia, monoethanolamine, 2-amino-2-methylpropanol, arginine, lysine, ornithine, and histidine.

In a particularly preferred embodiment, an agent according to the invention is characterized in that it contains at least one alkalizing agent (f) from the group consisting of ammonia, monoethanolamine, 2-amino-2-methylpropanol, arginine, lysine, ornithine, and histidine.

Within this group, the best results were obtained with ammonia and monoethanolamine. For this reason, the agents containing at least one alkalizing agent from the group consisting of ammonia and monoethanolamine, and very particularly preferably ammonia, are particularly preferred. Ammonia is most preferred.

In a particularly preferred embodiment, an agent according to the invention is therefore characterized in that it contains at least one alkalizing agent (f) from the group consisting of ammonia and monoethanolamine, and very particularly preferably ammonia.

By using the suitable or preferred alkalizing agent, the pH value introduced for the oxidative dyeing process can be adjusted in the dyeing agent according to the invention, which is in the range of 6.5 to 11.5, preferably 8.5 to 11.0, and very particularly preferably 9.0 to 10.5.

In the context of a particularly preferred embodiment, an agent according to the invention is thus characterized in that it contains water and has a pH of 6.5 to 11.5, preferably of 8.5 to 11.0, and very particularly preferably 9.0 to 10.5.

For precise adjustment of the pH, the dyeing agent can also contain one or more acidifying agents in addition to the alkalizing agents. According to the invention, preferred acidifying agents are edible acids, such as citric acid, acetic acid, malic acid, or tartaric acid, as well as dilute mineral acids. The pH values in the sense of the present invention are pH values which have been measured at a temperature of 22° C.

Additional Ingredients in the Agent

Preferably, an emulsifier or a surfactant is also added to the oxidative dyes, wherein surface-active substances are referred to as surfactants or emulsifiers depending upon the field of application and are selected from anionic, cationic, zwitterionic, amphoteric, and non-ionic surfactants and emulsifiers.

In a further very particularly preferred embodiment, an agent according to the invention is therefore characterized in that it contains at least one surfactant selected from the group consisting of anionic, amphoteric, zwitterionic, and non-ionic surfactants.

Suitable anionic surfactants in agents according to the invention are all anionic surface-active substances suitable for use on the human body. These are characterized by a water-solubilizing, anionic group, such as for example a carboxylate, sulfate, sulfonate, or phosphate group, and a lipophilic alkyl group having about 8 to 30 carbon atoms. In addition, glycol ether or polyglycol ether groups, ester, ether and amide groups, and hydroxyl groups can be contained in the molecule. Examples of suitable anionic surfactants are, in each case in the form of the sodium, potassium, and ammonium and mono-, di-, and trialkanolammonium salts having 2 to 4 carbon atoms in the alkanol group,

- linear and branched fatty acids having 8 to 30 C atoms (soaps),
- ether carboxylic acids of the formula $RO(CH_2CH_2O)_x CH_2COOH$, in which R is a linear alkyl group having 8 to 30 C atoms and x=0 or 1 to 16,
- acyl sarcosides having 8 to 24 C atoms in the acyl group,
- acyl taurides having 8 to 24 C atoms in the acyl group,
- acyl isethionates having 8 to 24 C atoms in the acyl group,
- sulfosuccinic acid mono- and dialkyl esters having 8 to 24 C atoms in the alkyl group and sulfosuccinic acid monoalkyl polyoxyethyl esters having 8 to 24 C atoms in the alkyl group and 1 to 6 oxyethyl groups,
- linear alkane sulfonates having 8 to 24 C atoms,
- linear α-olefin sulfonates having 8 to 24 C atoms,
- sulfonates of unsaturated fatty acids having 8 to 24 C atoms and 1 to 6 double bonds,
- α-sulfo fatty acid methyl esters of fatty acids having 8 to 30 C atoms,
- alkyl sulfates and alkyl ether sulfates of the formula $RO(CH_2CH_2O)_xSO_3H$, in which R is a preferably linear alkyl group having 8 to 30 C atoms and x=0 or 1 to 12,
- mixtures of surface-active hydroxy sulfonates,
- sulfated hydroxyalkyl polyethylene and/or hydroxyalkylene propylene glycol ethers
- esters of tartaric acid and citric acid with alcohols, which represent addition products of about 2-15 molecules of ethylene oxide and/or propylene oxide to fatty alcohols having 8 to 22 C atoms,
- alkyl and/or alkenyl ether phosphates of the formula

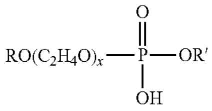

- in which R preferably represents an aliphatic, optionally unsaturated, hydrocarbon functional group having 8 to 30 carbon atoms, R' represents hydrogen, a functional group $(CH_2CH_2O)_yR$, and x and y independently of one another represent a number from 1 to 10,
- sulfated fatty acid alkylene glycol esters of formula $RC(O)O(alkO)_nSO_3H$, in which R represents a linear or branched, aliphatic, saturated and/or unsaturated alkyl functional group having 6 to 22 carbon atoms, alk represents $CH_2CH_2$, $CHCH_3CH_2$, and/or $CH_2CHCH_3$, and n represents a number from 0.5 to 5,
- monoglyceride sulfates and monoglyceride ether sulfates.

Preferred anionic surfactants are alkyl sulfates, alkyl ether sulfates, and ethercarboxylic acids having 10 to 18 carbon atoms in the alkyl group and up to 12 glycol ether groups in the molecule.

Surface-active compounds that carry, in the molecule, at least one quaternary ammonium group and at least one carboxylate, sulfonate, or sulfate group are referred to as zwitterionic surfactants. Particularly suitable zwitterionic surfactants are the so-called betaines, such as the N-alkyl-N,N-dimethylammonium glycinates, e.g., cocoalkyldimethylammonium glycinate, N-acylaminopropyl-N,N-dimethylammonium glycinates, e.g., cocoacylaminopropyldimethylammonium glycinate, and 2-alkyl-3-carboxymethyl-3-hydroxyethylimidazolines having in each case 8 to 18 carbon atoms in the alkyl or acyl group, and cocoacylaminoethylhydroxyethylcarboxymethyl glycinate. A preferred zwitterionic surfactant is the fatty acid amide derivative known by the INCI designation, cocamidopropyl betaine.

Amphoteric surfactants are understood to be surface-active compounds which, in addition to a $C_8$-$C_{24}$ alkyl or acyl group, also contain at least one free amino group and at least one —COOH— or —$SO_3H$ group in the molecule and are capable of forming inner salts. Examples of suitable amphoteric surfactants are N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids, and alkylaminoacetic acids having in each case about 8 to 24 carbon atoms in the alkyl group. Particularly preferred amphoteric surfactants are N-coco-alkylaminopropionate, coco-acylaminoethylaminopropionate, and $C_{12}$-$C_{18}$-acyl sarcosine.

It has also proven to be advantageous if the coloring and lightening agents according to the invention contain further, non-ionogenic surface-active substances. Non-ionic surfactants contain, as hydrophilic group, e.g., a polyol group, a polyalkylene glycol ether group, or a combination of polyol group and polyglycol ether group. Such compounds include, for example

- addition products of 1 to 50 mol ethylene oxide and/or 0 to 5 mol propylene oxide to linear and branched fatty alcohols having 8 to 30 carbon atoms, such as for example lauryl, myristyl, cetyl, but also stearyl, isostearyl, and oleyl alcohol, to fatty acids having 8 to 30 carbon atoms, and to alkylphenols having 8 to 15 carbon atoms in the alkyl group,

- addition products, end-capped with a methyl- or $C_2$-$C_6$ alkyl functional group, of 1 to 50 mol ethylene oxide and/or 0 to 5 mol propylene oxide to linear and branched fatty alcohols with 8 to 30 carbon atoms, to fatty acids with 8 to 30 carbon atoms, and to alkylphenols with 8 to 15 carbon atoms in the alkyl group, such as those types available under the trade names, Dehydol® LS, Dehydol® LT (Cognis),
- polyglycerol esters and alkoxylated polyglycerol esters, such as for example poly(3)glycerol diisostearate (commercial product:® LameformTGI (Henkel)) and poly(2)glycerol polyhydroxystearate (commercial product: Dehymuls® PGPH (Henkel)),
- polyol fatty acid esters, such as the commercially available product, Hydagen® HSP (Cognis) or Sovermol types (Cognis),
- more highly alkoxylated, preferably propoxylated, and in particular ethoxylated mono-, di-, and triglycerides, such as glycerol monolaurate+20 ethylene oxide and glycerol monostearate+20 ethylene oxide,
- amine oxides,
- hydroxy mixed ethers,
- sorbitan fatty acid esters and addition products of ethylene oxide to sorbitan fatty acid esters, such as polysorbates and sorbitol monolaurate+20 mol ethylene oxide (EO),
- sugar fatty acid esters and addition products of ethylene oxide to sugar fatty acid esters,
- addition products of ethylene oxide to fatty acid alkanolamides and fatty amines,
- fatty acid-N-alkyl glucamides,
- alkylphenols and alkylphenol alkoxylates having 6 to 21, and in particular 6 to 15, carbon atoms in the alkyl chain and 1 to 30 ethylene oxide and/or propylene oxide units. Preferred representatives of this class include nonylphenol+9 EO and octylphenol+8 EO,
- alkyl polyglycosides corresponding to the general formula RO—$(Z)_x$, where R denotes an alkyl, Z denotes a sugar, and x denotes the number of sugar units. Alkyl polyglycosides usable according to the present invention may contain only one specific alkyl functional group R. However, these compounds are normally prepared from natural fats and oils or mineral oils. In this case, the alkyl functional groups R are present as mixtures corresponding to the starting compounds or to the particular working-up of those compounds.

Particularly suitable non-ionic surfactants are $C_8$-$C_{22}$-alkyl monoglycosides and -alkyl oligoglycosides and their ethoxylated analogs. In particular, non-ethoxylated compounds have proven to be particularly suitable.

Particularly preferred are those alkyl polyglycosides of the formula RO—$(Z)_x$, where R

- substantially consists of $C_8$ and $C_{10}$ alkyl groups,
- substantially consists of $C_{12}$ and $C_{14}$ alkyl groups,
- substantially consists of $C_8$ to $C_{16}$ alkyl groups or
- substantially consists of $C_{12}$ to $C_{16}$ alkyl groups or
- substantially consists of $C_{16}$ to $C_{18}$ alkyl groups.

These compounds are characterized in that any mono- or oligosaccharides can be used as sugar building block Z. Usually, sugars with 5 or 6 carbon atoms as well as the corresponding oligosaccharides are used. Such sugars are, for example, glucose, fructose, galactose, arabinose, ribose, xylose, lyxose, allose, altrose, mannose, gulose, idose, talose, and sucrose. Preferred sugar building blocks are glucose, fructose, galactose, arabinose, and sucrose; glucose is particularly preferred.

The alkylpolyglycosides which can be used according to the invention contain on average 1.1 to 5 sugar units. Alkylpolyglycosides having x values of 1.1 to 2.0 are preferred. Very particular preference is given to alkylglycosides in which x is 1.1 to 1.8.

The alkoxylated homologs of said alkylpolyglycosides can also be used according to the invention. These homologs may contain on average up to 10 ethylene oxide and/or propylene oxide units per alkylglycoside unit.

Addition products of alkylene oxide to saturated linear fatty alcohols and fatty acids containing from 2 to 30 mol ethylene oxide per mol of fatty alcohol or acid have proved to be suitable as further preferred non-ionic surfactants. Preparations with excellent properties are likewise obtained if they contain fatty acid esters of ethoxylated glycerol as the non-ionic surfactants.

Particularly preferred non-ionogenic surface-active substances are, because of the simple processability, substances which are commercially available in pure form as solids or liquids. In this connection, the definition of purity does not refer to chemically pure compounds. Rather, in particular if products are natural-based products, mixtures of different homologs can be used, e.g., with different alkyl chain lengths, as are obtained in products based upon natural fats and oils. Mixtures of different degrees of alkoxylation are usually also present in alkoxylated products. In this context, the term, purity, actually refers to the fact that the selected substances should preferably be free of solvents, controls, and other accompanying substances.

Products with a "normal" homolog distribution as well as those with a narrow homolog distribution may be used as surfactants, which are addition products of ethylene and/or propylene oxide to fatty alcohols or derivatives of these addition products. "Normal" homolog distribution is to be understood in this case as mixtures of homologs which are obtained when reacting fatty alcohol and alkylene oxide using alkali metals, alkali metal hydroxides, or alkali metal alkoxides as catalysts. In contrast, a narrow homolog distribution is obtained when hydrotalcites, alkaline-earth metal salts of ether carboxylic acids, alkaline-earth metal oxides, hydroxides, or alkoxides for example are used as catalysts. The use of products with a narrow homolog distribution range may be preferred.

The anionic, non-ionic, zwitterionic, or amphoteric surfactants are used in amounts of 0.1 to 45 wt %, preferably 1 to 30 wt %, and very particularly preferably 1 to 15 wt %, relative to the total amount of the ready-to-use agent.

Also preferred according to the invention are cationic surfactants of the quaternary ammonium compound, esterquat, and amidoamine type. Preferred quaternary ammonium compounds are ammonium halides, and in particular chlorides and bromides, such as alkyl trimethyl ammonium chlorides, dialkyl dimethyl ammonium chlorides, and trialkyl methyl ammonium chlorides, e.g., cetyl trimethyl ammonium chloride, stearyl trimethyl ammonium chloride, distearyl dimethyl ammonium chloride, lauryl dimethyl ammonium chloride, lauryl dimethyl benzyl ammonium chloride, and tricetyl methyl ammonium chloride, and the imidazolium compounds known under the INCI names, Quaternium-27 and Quaternium-83. The long alkyl chains of the aforementioned surfactants preferably have 10 to 18 carbon atoms. The quaternized protein hydrolysates represent other cationic surfactants that can be used according to the invention.

The alkylamidoamines are usually prepared by amidation of natural or synthetic fatty acids and fatty acid fractions with dialkylaminoamines and are characterized by their good biodegradability alongside a good conditioning effect. One compound from this substance group which is particularly suitable according to the invention is the stearamidopropyl dimethylamine available commercially under the name, Tegoamid® S 18.

Also highly biodegradable are quaternary ester compounds—so-called "esterquats." Esterquats are known substances that contain both at least one ester function and at least one quaternary ammonium group as structural element. Preferred esterquats are quaternized ester salts of fatty acids with triethanolamine, quaternized ester salts of fatty acids with diethanolalkylamines, and quaternized ester salts of fatty acids with 1,2-dihydroxypropyldialkylamines. Such products are sold for example under the trademarks, Stepantex®, Dehyquart®, and Armocare®. The products, Armocare® VGH-70, an N,N-bis(2-palmitoyloxyethyl)dimethylammonium chloride, and Dehyquart® F-75, Dehyquart® C-4046, Dehyquart® L80, and Dehyquart® AU-35 are examples of such esterquats.

The cationic surfactants are contained in the agents used according to the invention preferably in amounts of 0.05 to 10 wt %, relative to the total agent. Particular preference is given to amounts of 0.1 to 5 wt %.

In one preferred embodiment, preference may be given to non-ionic, zwitterionic, and/or amphoteric surfactants and mixtures thereof.

In a further preferred embodiment, the effect of the active ingredient according to the invention can be enhanced by emulsifiers. Such emulsifiers are, for example,

- addition products of 4 to 30 mol of ethylene oxide and/or 0 to 5 mol of propylene oxide to linear fatty alcohols having 8 to 22 C atoms, to fatty acids having 12 to 22 C atoms, and to alkylphenols having 8 to 15 C atoms in the alkyl group,
- $C_{12}$-$C_{22}$ fatty acid monoesters and diesters of addition products of 1 to 30 mol of ethylene oxide to polyols having 3 to 6 carbon atoms, and in particular to glycerol,
- ethylene oxide and polyglycerol addition products to methyl glucoside fatty acid esters, fatty acid alkanolamides, and fatty acid glucamides,
- $C_8$-$C_{22}$ alkyl mono- and oligoglycosides and the ethoxylated analogs thereof, preference being given to degrees of oligomerization of 1.1 to 5, and in particular 1.2 to 2.0, and glucose as the sugar component,
- mixtures of alkyl (oligo)glucosides and fatty alcohols—for example, the commercially available product, Montanov® 68,
- addition products of 5 to 60 mol ethylene oxide to castor oil and hydrogenated castor oil,
- partial esters of polyols having 3 to 6 carbon atoms with saturated fatty acids having 8 to 22 carbon atoms,
- sterols, wherein sterols are understood to mean a group of steroids which carry a hydroxyl group on carbon atom 3 of the steroid backbone and are isolated both from animal tissue (zoosterols) and plant fats (phytosterols). Examples of zoosterols include cholesterol and lanosterol. Examples of suitable phytosterols include ergosterol, stigmasterol, and sitosterol. There are also sterols that are isolated from fungi and yeasts (the so-called mycosterols).
- phospholipids, and especially glucose phospholipids, which are obtained, for example, as lecithins or phosphatidylcholines from, for example, egg yolk or plant seeds (for example, soybeans),
- fatty acid esters of sugars and sugar alcohols, such as sorbitol,
- polyglycerols and polyglycerol derivatives, such as for example polyglycerol poly-12-hydroxystearate (commercial product: Dehymuls® PGPH)
- linear and branched fatty acids having 8 to 30 carbon atoms, and the Na, K, ammonium, Ca, Mg, and Zn salts thereof.

The agents according to the invention contain the emulsifiers preferably in amounts of 0.1 to 25 wt %, and in particular 0.5 to 15 wt %, relative to the total amount of the ready-to-use agent.

According to the invention, particular preference may be given to non-ionogenic emulsifiers and surfactants having an HLB value of 10-15. Among these emulsifier types, very particular preference may be given to those emulsifiers which contain no ethylene oxide and/or propylene oxide in the molecule.

Further work has shown that the oxidative formation of intense colorations from the components (a) and (b) functions in particular in the cosmetic carrier formulations the fat component content of which is not excessively high. A strong color application was then observed in particular if, relative to the total weight of the agent, the total amount of the fat components contained in the agent was below 25 wt %, preferably below 20 wt %, more preferably below 15 wt %, and very particularly preferably below 13 wt %.

In a further preferred embodiment, an agent according to the invention is characterized in that, relative to the total weight of the agent, the total amount of fat components contained in the agent is below 25 wt %, preferably below 20 wt %, further preferably below 15 wt %, and very particularly preferably below 13 wt %.

Fat components in the sense of the invention are understood to be organic compounds with a solubility in water of less than 1 wt %, and preferably less than 0.1 wt %, at room temperature (22° C.) and atmospheric pressure (760 mmHg).

Under the definition of fat components fall explicitly only uncharged (i.e., non-ionic) compounds. Fat components have at least one saturated or unsaturated alkyl group having at least 8 C atoms. The molecular weight of the fat component is at most 5,000 g/mol, preferably at most 2,500 g/mol, and particularly preferably at most 1,000 g/mol. The fat components are either polyoxyalkylated or polyglycerylated compounds.

In this connection, the components from the group of $C_{12}$-$C_{30}$ fatty alcohols, $C_{12}$-$C_{30}$ fatty acid triglycerides, and/or hydrocarbons are understood as fat components. In the sense of the present invention, only non-ionic substances are explicitly considered fat components. Charged compounds, such as fatty acids and salts thereof, are not understood to be fat components. $C_{12}$-$C_{30}$ fatty alcohols can be saturated, mono- or polyunsaturated, linear or branched fatty alcohols having 12 to 30 C atoms.

Examples of preferred linear saturated $C_{12}$-$C_{30}$ fatty alcohols are dodecan-1-ol (dodecyl alcohol, lauryl alcohol), tetradecan-1-ol (tetradecyl alcohol, myristyl alcohol), hexadecan-1-ol (hexadecyl alcohol, cetyl alcohol, palmityl alcohol), octadecan-1-ol (octadecyl alcohol, stearyl alcohol), arachyl alcohol (eicosan-1-ol), heneicosyl alcohol (heneicosan-1-ol), and/or behenyl alcohol (docosan-1-ol).

Linear, unsaturated fatty alcohols are (9Z)-octadec-9-en-1-ol (oleyl alcohol), (9E)-octadec-9-en-1-ol (elaidyl alcohol), (9Z,12Z)-octadeca-9,12-dien-1-ol (linoleyl alcohol), (9Z,12Z, 15Z)-octadeca-9,12,15-trien-1-ol (linolenoyl alcohol), gadoleyl alcohol ((9Z)-eicos-9-en-1-ol), arachidone alcohol ((5Z,8Z,11Z,14Z)-eicosa-5,8,11,14-tetraen-1-ol), erucyl alcohol ((13Z)-docos-13-en-1-ol), and/or brassidyl alcohol ((13E)-docosen-1-ol).

A $C_{12}$-$C_{30}$ fatty acid triglyceride is, in the sense of the present invention, understood as the triester of the trivalent alcohol glycerol with three equivalents of fatty acid. Both structurally similar and different fatty acids may be involved in the ester formation within a triglyceride molecule.

According to the invention, fatty acids are to be understood as saturated or unsaturated, unbranched or branched, unsubstituted or substituted $C_{12}$-$C_{30}$ carboxylic acids. Unsaturated fatty acids may be mono-unsaturated or poly-unsaturated. With an unsaturated fatty acid, the C—C double bond(s) thereof may have the cis or trans configuration.

Esters originating from glycerol and having a fatty acid, for example, can be referred to as fatty acid triglycerides, wherein the fatty acid is selected from dodecanoic acid (lauric acid), tetradecanoic acid (myristic acid), hexadecanoic acid (palmitic acid), tetracosanoic acid (lignoceric acid), octadecanoic acid (stearic acid), eicosanoic acid (arachidic acid), docosanoic acid (behenic acid), petroselinic acid [(Z)-6-octadecenoic acid], palmitoleic acid [(9Z)-hexadec-9-enoic acid], oleic acid [(9Z)-octadec-9-enoic acid], elaidic acid [(9E)-octadec-9-enoic acid], erucic acid [(13Z)-docos-13-enoic acid], linoleic acid [(9Z,12Z)-octadeca-9,12-dienoic acid], linolenic acid [(9Z,12Z,15Z)-octadeca-9,12,15-trienoic acid], eleostearic acid [(9Z,11E,13E)-octadeca-9,11,3-trienoic acid], arachidonic acid [(5Z,8Z,11Z,14Z)-eicosa-5,8,11,14-tetraenoic acid], and/or nervonic acid [(15Z)-tetracos-15-enoic acid].

The fatty acid triglycerides may also be of natural origin. The fatty acid triglycerides or mixtures thereof, e.g., corresponding natural fatty acid triglycerides, derived from soybean oil, peanut oil, olive oil, sunflower oil, macadamia nut oil, moringa oil, apricot kernel oil, marula oil, and/or optionally hydrogenated castor oil.

Hydrocarbons are compounds having 8 to 80 C atoms composed exclusively of carbon and hydrogen atoms. Especially preferred in this connection are aliphatic hydrocarbons, such as mineral oils, liquid paraffin oils (e.g., paraffinum liquidum or paraffinum perliquidum), isoparaffin oils, semisolid paraffin oils, paraffin waxes, solid paraffin (paraffinum solidum), Vaseline, and polydecene.

In this connection, liquid paraffin oils (paraffinum liquidum and paraffinum perliquidum) have proven to be particularly suitable. The hydrocarbon is very particularly preferably paraffinum liquidum, also referred to as white oil. Paraffinum liquidum is a mixture of purified, saturated, aliphatic hydrocarbons, consisting mainly of hydrocarbon chains having a C-chain distribution of 25 to 35 C atoms.

Furthermore, it has proved advantageous if the according to the invention contain at least one stabilizer or complexer. Conventional complexing agents and stabilizers that are preferred in the context of the present invention are, for example, polyoxycarboxylic acids, polyamines, ethylenediaminetetraacetic acid (EDTA), N-hydroxyethylethylenediaminetriacetic acid, diethylenetriaminepentaacetic acid (DTPA), ethylenediaminedisuccinic acid (EDDS), hydroxyethyliminodiacetic acid, nitridodiacetic acid-3-propionic acid, isoserindiacetic acid, N,N-di-(2-hydroxyethyl)glycine, N-(1,2-dicarboxy-2-hydroxyethyl)glycine, N-(1,2-dicarboxy-2-hydroxyethyl)aspartic acid or nitrilotriacetic acid (NTA), ethylenediaminediglutaric acid (EDGA), 2-hydroxypropylenediaminedisuccinic acid (HPDS), glycinamide-N,N'-disuccinic acid (GADS), ethylenediamine-N-N'-diglutaric acid (EDDG), 2-hydroxypropylenediamine-N-N'-disuccinic acid (HPDDS), diaminoalkyldi-(sulfosuccinic acid) (DDS), ethylenedicysteic acid (EDC), ethylenediamine-N-N'-bis-(ortho-hydroxyphenyl)acetic acid (EDDHA), N-2-hydroxyethylamine-N,N-diacetic acid, glyceryliminodiacetic acid, iminodiacetic acid-N-2-hydroxypropylsulfonic acid, aspartic acid-N-carboxymethyl-N-2,5-hydroxypropyl-3-sulfonic acid, β-alanine-N,N'-diacetic acid, aspartic acid-N,N'-diacetic acid, aspartic acid-N-monoacetic acid, dipicolinic acid, and salts and/or derivatives thereof, geminal diphosphonic acids such as 1-hydroxyethane-1,1-diphosphonic acid (HEDP), the higher homologs thereof with up to 8 carbon atoms, and also derivatives hereof containing hydroxy or amino groups and 1-aminoethane-1,1-diphosphonic acid, the higher homologs thereof with up to 8 carbon atoms, and also derivatives containing hydroxy or amino groups, aminophosphonic acids such as ethylenediamine tetra(methylene phosphonic acid) (EDTMP), diethylenetriamine penta(methylene phosphonic acid) (DTPMP) and higher homologs thereof, or nitrilo-tri(methylene phosphonic acid), phosphonopolycarboxylic acids such as 2-phosphonobutane-1,2,4-tricarboxylic acid, cyclodextrins, and alkali stannates (sodium stannate), alkalipyrophosphates (tetrasodiumpyrophosphate, disodiumpyrophosphate), alkaliphosphates (sodium phosphate), and phosphoric acid and salts thereof.

In the alkali pH values, required according to the invention, of the treatment solutions, these complexers are present at least partially as anions. It does not matter whether they are introduced in the form of acids or in the form of salts. In the case of use as salts, preference is given to alkali, ammonium, or alkylammonium salts, and in particular sodium salts.

Complexers preferred according to the invention are nitrogen-containing polycarboxylic acids, and in particular EDTA, and phosphonates, preferably hydroxyalkane or aminoalkane phosphonates, and in particular 1-hydroxyethane-1,1-diphosphonate (HEDP) or the di- or tetrasodium salt thereof, and/or ethylenediaminetetramethylenephosphonate (EDTMP) or the hexasodium salt thereof, and/or diethylenetriaminepentamethylenephosphonate (DTPMP) or the hepta- or octasodium salt thereof.

The dyes according to the invention can preferably contain further auxiliary substances and additives. For instance, it has proven preferable according to the invention if the agents contain at least one thickening agent. There are no basic restrictions with regard to these thickeners. Both organic and purely inorganic thickeners may be used.

According to a first preferred embodiment, the thickening agent is an anionic, synthetic polymer. Preferred anionic groups are the carboxylate group and the sulfonate group.

Examples of anionic monomers, which the polymeric anionic thickener may consist of, are acrylic acid, methacrylic acid, crotonic acid, itaconic acid, maleic anhydride, and 2-acrylamido-2-methylpropanesulfonic acid. Here, the acidic groups may be present wholly or partly as sodium-, potassium-, ammonium-, mono-, or triethanolammonium salt. Preferred monomers are maleic acid anhydride, and in particular, 2-acrylamido-2-methylpropane sulfonic acid and acrylic acid.

Preferred anionic homopolymers are uncrosslinked and crosslinked polyacrylic acids. Here, allyl ethers of pentaerythritol, sucrose, and propylene may be preferred crosslinking agents. Such compounds are commercially available, for example, under the trade name, Carbopol®. Also preferred is the homopolymer of 2-acrylamido-2-methyl propane sulfonic acid, which is commercially available, for example, under the name, Rheothik® 11-80.

Within this first embodiment, it may further be preferred to use copolymers of at least one anionic monomer and at least one non-ionic monomer. With regard to the anionic monomers, reference is made to the substances listed above. Preferred non-ionic monomers are acrylamide, methacrylamide, acrylic acid esters, methacrylic acid esters, itaconic acid monoesters and diesters, vinyl pyrrolidinone, vinyl ethers, and vinyl esters.

The anionic acrylic acid and/or methacrylic acid polymers or copolymers are contained in the agents according to the invention preferably in an amount of 0.1 to 10 wt %, and particularly preferably 1 to 5 wt %, in each case relative to the weight of the agent.

Preferred anionic copolymers are, for example, copolymers of acrylic acid, methacrylic acid or their $C_1$-$C_6$ alkyl esters, such as are marketed under the INCI name, acrylate copolymers. One preferred commercial product is Aculyn® 33 from Rohm & Haas, for example. However, copolymers of acrylic acid, methacrylic acid, or their $C_1$-$C_6$ alkyl esters and the esters of an ethylenically unsaturated acid and an alkoxylated fatty alcohol are further preferred. Suitable ethylenically unsaturated acids are in particular acrylic acid, methacrylic acid, and itaconic acid; suitable alkoxylated fatty alcohols are in particular Steareth-20 or Ceteth-20. Such copolymers are marketed by Rohm & Haas under the trade name, Aculyn® 22, and by National Starch under the trade names, Structure® 2001 and Structure® 3001.

Further preferred anionic copolymers are acrylic acid-acrylamide-copolymers as well as, in particular, polyacrylamide copolymers with monomers containing sulfonic acid groups. A particularly preferred anionic copolymer consists of 70 to 55 mol % acrylamide and 30 to 45 mol % 2-acrylamido-2-methylpropane sulfonic acid, wherein the sulfonic acid group is wholly or partially present as sodium-, potassium-, ammonium-, mono-, or triethanolammonium salt. This copolymer can also be crosslinked, wherein preferably polyolefinically unsaturated compounds such as tetraallyloxythane, allylsucrose, allylpentaerythritol, and methylene-bisacrylamide are used as crosslinking agents. Such a polymer is contained in the commercial products, Sepigel® 305 and Simulgel® 600 from the company, SEPPIC. The use of these compounds, which contain a hydrocarbon mixture ($C_{13}$-$C_{14}$ isoparaffin or isohexadecane) and a non-ionic emulsifier (laureth-7 or polysorbate-80) in addition to the polymer components, has proved to be particularly advantageous in the context of the teaching of the invention.

Also, polymers of maleic acid anhydride and methyl vinyl ether, and in particular those with crosslinks, are preferred thickeners. The maleic acid methyl-vinyl ether-copolymer crosslinked with 1,9-decadiene is available under the name, Stabileze® QM.

According to another embodiment, the thickener is a cationic synthetic polymer. Preferred cationic groups are quaternary ammonium groups. In particular, those polymers in which the quaternary ammonium group is bonded to a polymer backbone built-up of acrylic acid, methacrylic acid, or derivatives thereof via a $C_1$-$C_4$ hydrocarbon group have been found to be particularly suitable.

Homopolymers of general formula (HP-1), (HP-1)

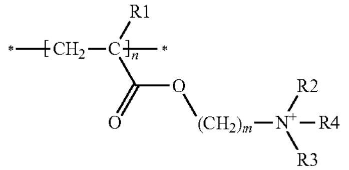

in which R1=—H or —$CH_3$, R2, R3, and R4 independently of one another are selected from $C_1$-$C_4$ alkyl, alkenyl, or hydroxyalkyl groups, m=1, 2, 3, or 4, n is a natural number, and $X^-$ is a physiologically tolerated organic or inorganic anion, as well as copolymers consisting substantially of the monomer units shown in formula (HP-1) and non-ionogenic monomer units, are particularly preferred cationic polymeric gel formers. In the context of these polymers, those are preferred according to the invention for which at least one of the following conditions applies:

R1 represents a methyl group,

R2, R3, and R4 are methyl groups, m has the value 2,

As a physiologically tolerated counter ion $X^-$, for example, halide ions, sulfate ions, phosphate ions, methosulfate ions, as well as organic ions such as lactate-, citrate-, tartrate-, and acetate ions may be considered. Halide ions are preferred—particularly chloride.

A particularly homopolymer is the suitable poly(methacryloxyethyltrimethylammonium) chloride (crosslinked, if desired) having the INCI name, Polyquaternium-37. The crosslinking can be carried out, if desired, with the help of olefinically poly-unsaturated compounds, e.g., divinylbenzene, tetraallyloxyethane, methylene bisacrylamide, diallyl ether, polyallyl polyglyceryl ether, or allyl ethers of sugars or sugar derivatives such as erythritol, pentaerythritol, arabitol, mannitol, sorbitol, sucrose, or glucose. Methylene bisacrylamide is a preferred crosslinking agent.

The homopolymer is preferably used in the form of a non-aqueous polymer dispersion, which should not have a polymer content of less than 30 wt %. Such polymer dispersions are commercially available under the names, Salcare® SC 95 (approx. 50% polymer content, further components: mineral oil (INCI name: mineral oil) and tridecyl-polyoxypropylene polyoxyethylene ether (INCI name: PPG-1-trideceth-6)) and Salcare® SC 96 (approx. 50% polymer content, further components: mixture of diesters of propylene glycol with a mixture of caprylic and capric acid (INCI name: propylene glycol dicaprylate/dicaprate) and tridecyl-polyoxypropylene polyoxyethylene ether (INCI name: PPG-1-trideceth-6)).

Copolymers having monomer units according to formula (HP-1) contain as non-ionogenic monomer units preferably acrylamide, methacrylamide, acrylic acid $C_1$-$C_4$ alkyl ester, and methacrylic acid $C_1$-$C_4$ alkyl ester. Among these non-ionic monomers, acrylamide is particularly preferred. These copolymers can also be crosslinked like the homopolymers described above. A preferred copolymer according to the invention is a crosslinked acrylamide methacroyl oxyethyl trimethyl ammonium chloride copolymer. Such copolymers, in which the monomers are present in a weight ratio of about 20:80, are commercially available as approx. 50% non-aqueous polymer dispersion under the name, Salcare® SC 92.

However, non-ionic, fully-synthetic polymers, such as for example polyvinyl alcohol or polyvinylpyrrolidone, can also be used as optionally additional thickening agents. Preferred non-ionic, fully-synthetic polymers are marketed for example by the company BASF under the trade name, Luviskol®. Such non-ionic polymers also allow, in addition to their excellent thickening properties, a significant improvement in the sensory feeling of the resulting preparations.

As inorganic thickeners, phyllosilicates (polymeric, crystalline sodium disilicates) have proven to be particularly suitable in the sense of the present invention. In particular, tone, and in particular, magnesium aluminum silicates, such as bentonite, and particularly smectites, such as montmorillonite or hectorite, which may also be optionally suitably modified, and synthetic phyllosilicates, such as the magnesium phyllosilicates marketed by the company Süd Chemie under the trade name, Optigel®, are preferred.

To further increase the performance of the oxidative dyeing agents, preferably at least one, optionally hydrated, $SiO_2$ compound is additionally added. It may be preferred according to the invention to use the optionally hydrated $SiO_2$ compounds in amounts of 0.05 wt % to 15 wt %, particularly preferably in amounts of 0.15 wt % to 10 wt %, and very particularly preferably in amounts of 0.2 wt % to 5 wt %, in each case relative to the agent according to the invention. The specified amounts in each case reflect here the content of the $SiO_2$ compounds (without the water content thereof) in the agents.

With regard to the optionally hydrated $SiO_2$ compounds, the present invention is in principle subject to no limitations. Preference is given to silicic acids, oligomers thereof and polymers thereof, and also salts thereof. Preferred salts are the alkali metal salts, and in particular the potassium and sodium salts. The sodium salts are very particularly preferred.

The optionally hydrated $SiO_2$ compounds may be present in different forms. According to the invention, preference is given to using the $SiO_2$ compounds in the form of silica gels, or particularly preferably as water glass. These $SiO_2$ compounds may sometimes be present in aqueous solution.

Very particularly preferred according to the invention are water glasses formed from a silicate of formula $(SiO_2)_n(Na_2O)_m(K_2O)_P$, where n represents a positive rational number, and m and p, independently of one another, represent a positive rational number or 0, with the proviso that at least one of the parameters m or p be different from 0, and the ratio between n and the sum of m and p be between 1:4 and 4:1. Preference is given to metasilicates in which the ratio between n and the sum of m and p is 1:2 or below.

Besides the components described by the empirical formula, the water glasses may also contain further additives in small amounts, such as for example phosphates or magnesium salts.

Water glasses which are particularly preferred according to the invention are marketed among others by the company Henkel under the names, Ferrosil® 119, Natronwasserglas 40/42, Portil® A, Portil® AW, and Portil® W, and by the company Akzo under the name, Britesil® C20.

The oxidative dyeing agents are preferably packaged as flowable preparations.

The agents according to the invention may also contain further active substances, auxiliaries, and additives, such as for example,

- non-ionic polymers, such as for example vinylpyrrolidinone/vinyl acrylate copolymers, polyvinylpyrrolidinone, vinylpyrrolidinone/vinyl acetate copolymers, polyethylene glycols, and polysiloxanes,
- silicones such as volatile or non-volatile, straight-chain, branched or cyclic, crosslinked or non-crosslinked polyalkylsiloxanes (such as dimethicones or cyclomethicones), polyarylsiloxanes and/or polyalkylarylsiloxanes, and in particular polysiloxanes having organofunctional groups, such as substituted or unsubstituted amines (amodimethicones), carboxyl, alkoxy, and/or hydroxyl groups (dimethicone copolyols), linear polysiloxane (A)/polyoxyalkylene (B) block copolymers, grafted silicone polymers having a non-silicone-containing organic backbone or having a polysiloxane backbone, such as for example the commercial product, Abil B 8832, from the company Degussa, which is marketed under the INCI name, Bis-PEG/PPG-20/20 Dimethicone, or mixtures thereof,
- cationic polymers such as quaternized cellulose ethers, polysiloxanes with quaternary groups, dimethyldiallylammonium chloride polymers, acrylamide-dimethyldiallylammonium chloride copolymers, dimethylaminoethylmethacrylate-vinylpyrrolidinone copolymers quaternized with diethyl sulfate, vinylpyrrolidinone-imidazolinium-methochloride copolymers, and quaternized polyvinyl alcohol,
- structurants, such as glucose, maleic acid, and lactic acid,
- hair-conditioning compounds such as phospholipids, e.g., soya lecithin, egg lecithin, and cephalins, as well as silicone oils,
- perfume oils, dimethyl isosorbide, and cyclodextrins,
- solvents and solubilizers such as ethanol, isopropanol, ethylene glycol, propylene glycol, glycerol, and diethylene glycol,
- fiber-structure-improving active ingredients, and in particular mono-, di-, and oligosaccharides such as glucose, galactose, fructose, fruit sugar, and lactose,
- quaternized amines such as methyl-1-alkylamidoethyl-2-alkylimidazolinium methosulfate,
- defoaming agents such as silicones,
- dyes for coloring the agent,
- anti-dandruff active substances such as piroctone olamine, zinc omadine, and climbazole,
- amino acids and oligopeptides, and in particular arginine and/or serine,
- protein hydrolysates of animal and/or plant origin, such as elastin, collagen, keratin, silk, and lactoprotein protein hydrolysates, or almond, rice, pea, potato, and wheat protein hydrolysates, as well as those in the form of their fatty acid condensation products or optionally anionically- or cationically-modified derivatives thereof,
- vegetable oils, e.g., macadamia nut oil, kukui nut oil, palm oil, amaranth seed oil, peach kernel oil, avocado oil, olive oil, coconut oil, rapeseed oil, sesame oil, jojoba oil, soybean oil, peanut oil, evening primrose oil, and tea tree oil,
- light stabilizers, and in particular derivatized benzophenones, cinnamic acid derivatives, and triazines,
- substances for adjusting the pH, such as for example conventional acids, and in particular edible acids and bases,
- active substances such as panthenol, pantothenic acid, pantolactone, allantoin, pyrrolidinone carboxylic acids and the salts thereof, and bisabolol,
- polyphenols, and in particular hydroxycinnamic acids, 6,7-dihydroxycoumarin, hydroxybenzoic acids, catechins, tannins, leucoanthocyanidins, anthocyanidins, flavanones, flavones, and flavonols,
- ceramides, and preferably the sphingolipids such as ceramide I, ceramide II, ceramide 1, ceramide 2, ceramide 3, ceramide 5, and ceramide 6, or pseudoceramides, such as in particular N—($C_8$-$C_{22}$-Acyl)-($C_8$-$C_{22}$-acyl)-hydroxyproline,
- vitamins, provitamins, and vitamin precursors, and in particular those of groups A, $B_3$, $B_5$, $B_6$, C, E, F, and H,
- plant extracts such as for example the extracts of aloe vera, angelica, anise, apricot, benzoin, bergamot, birch, nettle, calamus, blackcurrant, costus, hibiscus, oak bark, elemi, tarragon, pine needles, galbanum, geranium, ginseng, grapefruit, guaiac wood, green tea, hamamelis, restharrow, hops, coltsfoot, ginger root, iris, jasmine, chamomile, cardamom, clover, burdock root, pine, kiwi fruit, coconut, coriander, caraway, mountain pine, lavender, lemon grass, lily, lime, linden blossom, lychee, mace, malva, almond, mango, lemon balm, melon, meristem, myrrh, neroli, olibanum, opoponax, orange, patchouli, petitgrain, stone pine, wild thyme, rooibos, rose, rosemary, horse chestnut, sandalwood, sage, horsetail, yarrow, celery, spruce, thyme, juniper, vine leaves, hawthorn, wheat, lady's-smock, ylang-ylang, cedar, and lemon, cholesterol, consistency regulators such as sugar esters, polyol esters, or polyol alkyl ethers, fats and waxes such as spermaceti, beeswax, Montan wax, and paraffins, fatty acid alkanolamides, swelling and penetration agents such as glycerol, propylene glycol monoethyl ether, carbonates, hydrogen carbonates, guanidines, ureas, and primary, secondary, and tertiary phosphates, turbidity agents such as latex, styrene/PVP, and styrene/acrylamide copolymers, pearlescent agents such as ethylene glycol mono- and distearate and PEG-3 distearate, pigments, stabilizing agent for hydrogen peroxide and other oxidizing agents, propellants such as propane-butane mixtures, $N_2O$, dimethyl ether, $CO_2$, and air, antioxidants.

The selection of these additional substances is made by the person skilled in the art according to the desired properties of the agents. With respect to other optional components and the employed amounts of said components, reference is made expressly to relevant manuals known to the person skilled in the art, e.g., Kh. Schrader, *Grundlagen und Rezepturen der Kosmetika,* 2nd edition, Hüthig Buch Verlag, Heidelberg, 1989. The additional active ingredients and auxiliaries are used in the agents according to the invention preferably in quantities of, in each case, 0.0001 to 10 wt %, and in particular 0.0005 to 5 wt %, relative to the total weight of the application mixture.

Method for Oxidatively Dyeing Keratin Fibers

The oxidative dyeing agent according to the invention of the first subject matter of the invention is outstandingly suitable for use in corresponding dyeing methods.

A further subject matter of the present invention is therefore a method for the oxidative dyeing of keratin fibers, and in particular human hair, in which an agent, as disclosed in detail in the description of the first subject matter of the invention, is applied to the keratin fibers and rinsed out again after an exposure time.

While the fibers are being exposed to the agent, it can be advantageous to support the dyeing process by applying heat. Heat can be applied by an external heat source, such as hot air from a hot-air blower, and also, in particular in the case of dyeing the hair of a living subject, by the body temperature of the subject. In the latter possibility, conventionally, the part to be dyed is covered with a cap. In particular, the temperature during the exposure time is between 10°° C. and 45° C., and in particular between 20° C. and 40° C. The dyeing agents according to the invention already give intense colorations at physiologically tolerated temperatures of less than 45° C. Therefore they are suitable particularly for coloring human hair.

With respect to further preferred embodiments of the method according to the invention, what has been said about the agents according to the invention applies mutatis mutandis.

What is claimed is:

1. An agent for oxidatively dyeing keratinous fibers, the agent comprising, in a cosmetic carrier:

isatin;

at least one polymer selected from the group consisting of xanthan gum, algin, carrageenan, cetyl hydroxyethyl cellulose, carboxymethyl cellulose, tragacanth, gum karaya, gum ghatti, agar, chitin, chitosan, gum arabic, gellan, guar, tamarind seed flour, carob gum, and physiologically tolerated salts thereof; and at least one oxidation dye precursor of coupler type selected from the group consisting of 3-amino-2-chloro-6-methylphenol and 1-methoxy-2-amino-4-(2-hydroxyethylamino)benzene, wherein the agent is free of resorcinols.

2. The agent of claim 1, wherein the isatin is present in an amount of from 0.001 to 10 wt %, based on the total weight of the agent.

3. The agent of claim 2, wherein the isatin is present in an amount of from 0.1 to 3.5 wt %, based on the total weight of the agent.

4. The agent of claim 1, wherein the at least one polymer is selected from the group consisting of xanthan, algin, carrageenan, cetyl hydroxyethyl cellulose, carboxymethyl cellulose, and physiologically tolerated salts thereof.

5. The agent of claim 1, wherein the at least one polymer is present in an amount of from 0.01 to 10.0 wt %, based on the total weight of the agent.

6. The agent of claim 5, wherein the at least one polymer is present in an amount of from 0.2 to 2.5 wt %, based on the total weight of the agent.

7. The agent of claim 6, wherein the at least one polymer is present in an amount of from 0.3 to 1.5 wt %, based on the total weight of the agent.

8. The agent of claim 1, further comprising at least one oxidation dye precursor of developer type selected from the group consisting of p-toluenediamine, 2-methoxymethyl-p-phenylenediamine, 2-(2-hydroxyethyl)-p-phenylenediamine, N,N-bis-(2-hydroxyethyl)-p-phenylenediamine, p-phenylenediamine, 4-amino-3-methylphenol, p-aminophenol, 4,5-diamino-1-(2-hydroxyethyl) pyrazole, and the physiologically tolerated salts thereof.

9. The agent of claim 8, wherein the at least one oxidation dye precursor of developer type is present in an amount of from 0.001 to 10.0 wt %, based on the total weight of the agent.

10. The agent of claim 9, wherein the at least one oxidation dye precursor of developer type is present in an amount of 0.1 to 5.0 wt %, based on the total weight of the agent.

11. The agent of claim 1, wherein the at least one oxidation dye precursor of coupler type further comprises a second oxidation dye precursor of coupler type selected from the group consisting of 3-aminophenol, 5-amino-2-methylphenol, 2-hydroxy-4-aminophenoxyethanol, 5-amino-4-chloro-2-methylphenol, 5-(2-hydroxyethyl)-amino-2-methylphenol, 2,4-dichloro-3-aminophenol, 2-aminophenol, 3-phenylenediamine, 2-(2,4-diaminophenoxy) ethanol, 1,3-bis(2,4-diaminophenoxy) propane, 1,3-bis-(2,4-diaminophenyl) propane, 2,6-bis(2'-hydroxyethylamino)-1-methylbenzene, 1-amino-3-bis-(2-hydroxyethyl) aminobenzene, 2-amino-3-hydroxypyridine, 3-amino-2-methylamino-6-methoxypyridine, 2,6-dihydroxy-3,4- dimethylpyridine, 3,5-diamino-2,6-dimethoxypyridine, 1-phenyl-3-methyl pyrazol-5-one, 1-naphthol, 1,5-dihydroxynaphthalene, 2,7-dihydroxynaphthalene, 1,7-dihydroxynaphthalene, 1,8-dihydroxynaphthalene, 4-hydroxyindole, 6-hydroxyindole, 7-hydroxyindole, 4-hydroxyindolin, 6-hydroxyindolin, 7-hydroxyindolin, and/or 7-hydroxyindolin, any mixture thereof, and the physiologically tolerated salts thereof.

12. The agent of claim 1, wherein the at least one oxidation dye precursor of coupler type is present in an amount of from 0.001 to 10 wt %, based on the total weight of the agent.

13. The agent of claim 12, wherein the at least one oxidation dye precursor of coupler type is present in an amount of from 0.15 to 2.5 wt %, based on the total weight of the agent.

14. The agent of claim 1, further comprising at least one oxidizing agent selected from the group consisting of hydrogen peroxide, addition products of hydrogen peroxide to organic compounds, and addition products of hydrogen peroxide to inorganic compounds.

15. The agent of claim 1, further comprising at least one alkalizing agent selected from the group consisting of ammonia, monoethanolamine, 2-amino-2-methylpropanol, arginine, lysine, ornithine, and histidine.

16. The agent of claim 1, further comprising a surfactant selected from the group consisting of anionic surfactants, amphoteric surfactants, zwitterionic surfactants, and nonionic surfactants.

17. The agent of claim 1, further comprising a nonionogenic surfact-active substance having a hydrophilic group selected from group consisting of a polyol group, a polyalkylene glycol ether group, and a combination thereof.

18. The agent of claim 1, further comprising a cationic synthetic polymer.

* * * * *